United States Patent
Wang (10) Patent No.: US 9,895,241 B2
(45) Date of Patent: Feb. 20, 2018

(54) METHODS FOR CRIMPING A POLYMERIC STENT SCAFFOLD ONTO A DELIVERY BALLOON

(71) Applicant: Abbott Cardiovascular Systems Inc., Santa Clara, CA (US)

(72) Inventor: Yunbing Wang, Sunnyvale, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 693 days.

(21) Appl. No.: 14/280,476

(22) Filed: May 16, 2014

(65) Prior Publication Data
US 2014/0250667 A1 Sep. 11, 2014

Related U.S. Application Data

(62) Division of application No. 12/776,317, filed on May 7, 2010, now Pat. No. 8,844,113.

(51) Int. Cl.
*A61F 2/82* (2013.01)
*A61F 2/915* (2013.01)
(Continued)

(52) U.S. Cl.
CPC .............. *A61F 2/82* (2013.01); *A61F 2/915* (2013.01); *A61F 2/958* (2013.01);
(Continued)

(58) Field of Classification Search
CPC .. A61F 2/82; A61F 2/958; A61F 2/915; A61F 2002/9522; Y10T 29/49913; Y10T 29/49908
See application file for complete search history.

(56) References Cited

U.S. PATENT DOCUMENTS 5,836,965 A  11/1998  Jendersee et al.
5,913,871 A * 6/1999  Werneth ................. A61F 2/958
                                                  606/195

(Continued)

FOREIGN PATENT DOCUMENTS

EP    1 295 570       3/2003
WO    WO 99/55406    11/1999
(Continued)

OTHER PUBLICATIONS

U.S. Appl. No. 11/330,927, filed Jan. 11, 2006, Wu et al.
(Continued)

*Primary Examiner* — Peter DungBa Vo
*Assistant Examiner* — Jeffrey T Carley
(74) *Attorney, Agent, or Firm* — Squire Patton Boggs (US) LLP (57) ABSTRACT

A medical device includes a polymer stent scaffold crimped to a catheter having an expansion balloon. A process for forming the medical device includes placing the scaffold on a support supported by an alignment carriage, and deionizing the scaffold to remove any static charge buildup on the scaffold before placing the scaffold within a crimper to reduce the scaffold's diameter. The polymer scaffold is heated to a temperature below the polymer's glass transition temperature to improve scaffold retention without adversely affecting the mechanical characteristics of the scaffold when deployed to support a body lumen.

16 Claims, 3 Drawing Sheets

(51) Int. Cl.
*A61F 2/958* (2013.01)
*A61F 2/95* (2013.01)

(52) U.S. Cl.
CPC .............. *A61F 2002/91533* (2013.01); *A61F 2002/91566* (2013.01); *A61F 2002/9522* (2013.01); *A61F 2210/0071* (2013.01); *Y10T 29/49865* (2015.01); *Y10T 29/49885* (2015.01); *Y10T 29/49908* (2015.01); *Y10T 29/49909* (2015.01); *Y10T 29/49913* (2015.01); *Y10T 29/49915* (2015.01); *Y10T 29/49927* (2015.01); *Y10T 29/53657* (2015.01)

(56) References Cited

U.S. PATENT DOCUMENTS

| | | | |
|---|---|---|---|
| 5,976,181 | A | 11/1999 | Whelan et al. |
| 6,745,445 | B2 * | 6/2004 | Spilka ................ A61F 2/958 29/234 |
| 6,863,683 | B2 | 3/2005 | Schwager et al. |
| 7,761,968 | B2 | 7/2010 | Huang et al. |
| 7,951,185 | B1 | 5/2011 | Abbate et al. |
| 7,971,333 | B2 * | 7/2011 | Gale ................... A61F 2/91 219/121.67 |
| 2002/0143382 | A1 * | 10/2002 | Hijlkema ............. B29B 13/02 623/1.11 |
| 2004/0078953 | A1 | 4/2004 | Spilka |
| 2004/0106973 | A1 | 6/2004 | Johnson |
| 2005/0119720 | A1 | 6/2005 | Gale et al. |
| 2005/0283225 | A1 * | 12/2005 | Klisch ................ A61F 2/82 623/1.15 |
| 2006/0047336 | A1 | 3/2006 | Gale et al. |
| 2007/0006441 | A1 * | 1/2007 | McNiven ............ A61F 2/958 29/508 |
| 2007/0271763 | A1 | 11/2007 | Huang et al. |
| 2007/0282433 | A1 | 12/2007 | Limon et al. |
| 2007/0289117 | A1 | 12/2007 | Huang et al. |
| 2008/0016668 | A1 | 1/2008 | Huang et al. |
| 2008/0033523 | A1 | 2/2008 | Gale et al. |
| 2008/0033524 | A1 | 2/2008 | Gale |
| 2008/0147164 | A1 | 6/2008 | Gale et al. |
| 2008/0275537 | A1 * | 11/2008 | Limon ................ A61F 2/91 623/1.15 |
| 2009/0001633 | A1 | 1/2009 | Limon et al. |
| 2009/0088829 | A1 | 4/2009 | Wang et al. |
| 2009/0287289 | A1 | 11/2009 | Sagedahl et al. |
| 2010/0004735 | A1 | 1/2010 | Yang et al. |
| 2010/0025894 | A1 | 2/2010 | Kleiner et al. |

FOREIGN PATENT DOCUMENTS

| | | |
|---|---|---|
| WO | WO 2007/146354 | 12/2007 |
| WO | WO 2010/151497 | 12/2010 |

OTHER PUBLICATIONS

International Search Report and the Written Opinion for PCT/US2008/077108 dated Feb. 2, 2009, 6 pgs.
International Search Report and the Written Opinion for PCT/US2011/032283 dated Aug. 18, 2011, 17 pgs.

* cited by examiner

PRIOR ART

FIG. 5

METHODS FOR CRIMPING A POLYMERIC STENT SCAFFOLD ONTO A DELIVERY BALLOON

This application is a divisional of U.S. application Ser. No. 12/776,317 filed May 7, 2010, the entire contents of which are hereby incorporated by reference for all purposes.

BACKGROUND OF THE INVENTION

Field of the Invention

The present invention relates to drug-eluting medical devices; more particularly, this invention relates to processes for crimping a polymeric stent to a delivery balloon.

Background of the Invention

The art recognizes a variety of factors that affect a polymeric stent's ability to retain its structural integrity when subjected to external loadings, such as crimping and balloon expansion forces. These interactions are complex and the mechanisms of action not fully understand. According to the art, characteristics differentiating a polymeric, bio-absorbable stent scaffold of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing, or scaffold portion of a balloon-expandable stent. The models are not generally capable of providing an acceptable degree of certainty required for purposes of implanting the stent within a body, or predicting/anticipating the empirical data.

Moreover, it is recognized that the state of the art in medical device-related balloon fabrication, e.g., non-compliant balloons for stent deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed polymeric stent scaffold. One difference, for example, is the propensity for fracture or cracks to develop in a stent scaffold. The art recognizes the mechanical problem as too different to provide helpful insights, therefore, despite a shared similarity in class of material. At best, the balloon fabrication art provides only general guidance for one seeking to improve characteristics of a balloon-expanded, bio-absorbable polymeric stent.

Polymer material considered for use as a polymeric stent scaffold, e.g. PLLA or PLGA, may be described, through comparison with a metallic material used to form a stent scaffold, in some of the following ways. A suitable polymer has a low strength to weight ratio, which means more material is needed to provide an equivalent mechanical property to that of a metal. Therefore, struts must be made thicker and wider to have the strength needed. The scaffold also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA.

Processing steps performed on, and design changes made to a metal stent that have not typically raised concerns for, or required careful attention to unanticipated changes in the average mechanical properties of the material, therefore, may not also apply to a polymer stent due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after stent fabrication, e.g., crimping? As a consequence, a change to a fabrication process, post-fabrication process or even relatively minor changes to a stent pattern design must, generally speaking, be investigated more thoroughly than if a metallic material were used instead of the polymer. It follows, therefore, that when choosing among different polymeric stent designs for improvement thereof, there are far less inferences, theories, or systematic methods of discovery available, as a tool for steering one clear of unproductive paths, and towards more productive paths for improvement, than when making changes in a metal stent.

It is recognized, therefore, that, whereas inferences previously accepted in the art for stent validation or feasibility when an isotropic and ductile metallic material was used, such inferences would be inappropriate for a polymeric stent. A change in a polymeric stent pattern may affect not only the stiffness or lumen coverage of the stent in its deployed state supporting a lumen, but also the propensity for fractures to develop when the stent is crimped or being deployed. This means that, in comparison to a metallic stent, there is generally no assumption that can be made as to whether a changed stent pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric stent scaffold that is plastically deformed, both when crimped to, and when later deployed by a balloon, unfortunately, is not as easy to predict as a metal stent. Indeed, it is recognized that unexpected problems may arise in polymer stent fabrication steps as a result of a changed pattern that would not have necessitated any changes if the pattern was instead formed from a metal tube. In contrast to changes in a metallic stent pattern, a change in polymer stent pattern may necessitate other modifications in fabrication steps or post-fabrication processing, such as crimping and sterilization.

One problem encountered with a polymer stent is the stents susceptibility to damage when being crimped to a balloon. Non-uniform forces applied during a crimping process can cause irregular deformations in struts of a polymer stent, which can induce crack formation and loss of strength. There is a continuing need to improve upon the crimping methods, or pre-crimping procedures used for polymer stents to reduce instance of crack formation or irregular strut deformation during stent production.

SUMMARY OF THE INVENTION

The invention provides a process for crimping a polymer stent scaffold, or scaffold to a balloon. The polymer scaffold is expanded for placement within a lumen of the body by plastic deformation of the polymer scaffold of the scaffold. The crimping process used to place the scaffold on the balloon includes, in one embodiment, a pre-crimp and final crimp step.

It was discovered that polymer scaffolds are susceptible to damage if they have a slight misalignment with jaws of a crimper. A "slight" misalignment means a misalignment that the art has tolerated in the past and has assumed were present but not capable of significantly effecting how the scaffold would be deformed by the crimper as compared to the same scaffold when perfectly aligned with jaws of the crimper. Such misalignment tolerance will be understood by reference to information available from a manufacturer of a commercially available crimping device. The inventor discovered, unexpectedly, that if a "slight" misalignment is removed, or substantially removed, when crimping a polymer scaffold, there is a significant reduction in the irregular deformations of scaffold struts that are sufficient to cause irreparable damage to a polymer scaffold, e.g., a PLLA scaffold.

According to the invention, one or more improvements in alignment for a polymer scaffold are included in the crimping process as in, according to one embodiment, a pre-crimp process. Preparation for the pre-crimp process includes a deionizing step to remove static buildup on the polymer scaffold. By removing a static charge on the polymer material, the scaffold should sit more level on the support, i.e., a rod, mandrel or catheter, thereby improving alignment with the crimper. Additional measure may be employed. A carriage support for positioning the scaffold within the crimper includes a magnetic element for engagement with an end of the support holding the scaffold. The scaffold support is held to a surface of the base e.g., a grooved channel proximal to, or formed by the magnetic element, by a magnet force of attraction. When the surface of the base is aligned with the crimper, so too will the support align with the crimper. Less operator skill is required to align the scaffold. Slight misalignments causing damage when the polymer scaffold is crimped are, therefore, more often avoided. Existing devices for scaffold alignment, by contrast, use mechanical devices, e.g. lock knobs, that require adjustment, which can lead to more frequent misalignment problems.

A first and second carriage support may be used to support both ends, as opposed to only one end of the scaffold support. In this alternative embodiment, the two ends of the scaffold support are supported by contacting surfaces of the respective bases of the carriage supports and held thereto by a magnet force of attraction. Each base support is located on opposite ends of the crimper. Alternatively, only one of the bases may employ a magnet. The second base is provided so that the free end of the scaffold support may be supported in addition to the fixed end to provide better accuracy in alignment. The second base may provide a flat surface level with the surface of the first base support surface, or each may have grooves to receive the ends of the scaffold support, in precise alignment with the central axis of the crimper. This arrangement may further reduce requirements for operator skill when aligning the stent with the crimper, e.g., the operator need only place the ends of the scaffold support within the aligned grooves.

Supporting both ends of the scaffold also permits it to support more weight without deflecting, which causes misalignment. A scaffold support, supported by two movable rails preferably as fixed (i.e., 6 degree of freedom restraint at both ends), may also be used to perform a pre-crimping process for two stents. A first and second carriage, which move left to right or right to left along rails in unison, each support a scaffold on opposite sides of the crimper. In this arrangement a stent on one side of the crimper may be pre-crimped first, followed by the stent on the opposite side. Alternatively, stents may be disposed on the improved support so that two or more scaffolds may be crimped simultaneously. This increases production efficiency for a pre-crimp.

After being more suitably aligned, the polymer scaffold may be inserted into the crimper to reduce its diameter to a pre-crimp diameter. The reduced-diameter scaffold is then removed from the scaffold support, placed on, and aligned with the balloon of the delivery catheter. The scaffold is then crimped to a final crimped diameter on the balloon. Preferably, a multi-step final crimping process includes heating the scaffold to a temperature just below the glass transition temperature of the polymer to avoid damaging the scaffold when it is crimped and without significantly altering the scaffold's deployed strength/stiffness characteristics.

In one aspect of the invention there is a method for crimping a balloon-expanded stent scaffold to a balloon, comprising the steps of providing a tube; radially expanding the tube to increase its radial strength; forming the scaffold from the radially-expanded tube, including the steps of forming a circumferential series of closed cells having a W-shape and linear link struts connecting the W-shape cells. The scaffold is deionized and then the deionized scaffold is crimped to the balloon. Preferably the scaffold is deionized just prior to being inserted into the crimper to avoid damage to the scaffold when crimped.

In another aspect, there is a method for crimping a balloon-expanded polymer scaffold to a balloon using a crimper, comprising the steps of: performing a pre-crimp of the polymer scaffold to reduce the diameter of the scaffold before crimping the scaffold to the balloon. The pre-crimp steps include aligning a support with jaws of the crimper by affixing a first end of the support to a carriage having a surface adapted for supporting the first end of the support to the carriage by a magnetic force, disposing the polymer scaffold on a second end of the support, and deionizing the polymer scaffold. The deionized polymer scaffold is then placed in the crimper while supported on the support, and its diameter reduced. After this diameter reduction, the scaffold is crimped to the balloon.

In another aspect, there is a crimping system for a scaffold, including a crimper, a scaffold support having first and second ends, the scaffold being supported on the scaffold support, a first base support for supporting the first end, a second base support having a second end, wherein the first and second base supports are disposed on opposite sides of the crimper. Both base supports may have a magnet for holding the scaffold support ends.

The scope of the methods and apparatus of the invention also encompass processes that crimp a scaffold as substantially described in US Pub. No. 2010/0004735 and US Pub. No. 2008/0275537. The thickness of the tube from which the scaffold is formed may have a thickness of between 0.10 mm and 0.18 mm, and more narrowly at or about 0.152 mm. The scaffold may be made from PLLA. And the scaffold may be crimped to a PEBAX balloon.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

The invention arose out of a need to solve a problem of high rejection rates, for polymer scaffolds during a pre-crimp process that could not be explained, or cured by existing methods for diagnosing or solving, respectively, crimping problems. During a pre-crimp process, the scaffold diameter is reduced to a diameter intermediate of its starting diameter and a final crimped diameter on the balloon. After the scaffold's diameter has been reduced in diameter by the crimper, the scaffold is placed on a balloon of the delivery catheter and re-inserted into the crimper. The crimper reduces the scaffold diameter to its final, crimped diameter on the balloon. When reduced down to the final crimped diameter, there is a retention force between the scaffold and balloon for retaining the scaffold on the balloon. The disclosure refers to a stent "scaffold". It will be understood that the same processes and apparatus described herein apply to a balloon expandable "stent" that uses a scaffold as its load bearing structure.

For the pre-crimp phase of the process the scaffold is supported on a distal end of a scaffold support, such as a rod, mandrel or catheter. The proximal end of the scaffold support is held on a base support, which is relied on to align the scaffold support distal end, where the scaffold is located, with the jaws of the crimper so that the scaffold may be properly positioned within the crimper before it is deformed to its pre-crimp diameter. This process is carried out in an environment that is relatively sterile and having low humidity. As will be appreciated, when the scaffold is within the crimper and the crimping force applied, the interaction between surfaces of the scaffold and the crimper jaws as the scaffold is being deformed to a reduced diameter cannot be visually inspected. The scaffold's scaffold is being deformed within a cavity that completely blocks the scaffold from view. As such, an operator cannot identify irregular deformations of the scaffold as it is being deformed. A scaffold that, when deformed, develops irregularly bent, or twisted struts cannot be discovered until after it is removed from the crimper and visually inspected. At this point, irreparable damage has occurred and the scaffold is discarded.

As is generally known in the art, the nature of deformation of an article through externally applied forces may, in some situations, be inferred from the reaction forces applied by the article against the body, through which the external force is applied. For example, if the body applying the force to the article is programmed to enforce a displacement at a prescribed rate, monitoring the changes in the force needed to maintain the enforced displacement can give clues as to how the body is being deformed. In the case of a scaffold, an operator can set the rate for crimping and monitor the applied force. However, the known methods for instrumentation are not capable of providing the level of accuracy needed to infer how individual struts are being deformed by crimper jaws. The operator, therefore, has virtually knowledge about how the scaffold's struts are being deformed within the crimper. The only knowledge that the operator has about how the scaffold might have been deformed when in the crimper occurs when the scaffold is withdrawn from the crimper and visually inspected. Again, at this point irreparable damage has occurred and the scaffold is discarded.

The inventor was presented with the problem of a high proportion of polymer scaffolds being rejected because struts of the scaffold were being irregularly deformed during a pre-crimp process, and such irregularly deforming damage would potentially cause the fractures or broken struts during polymeric stent deployment. Scaffold strength and stiffness concerns raised by the appearance of irregular deformations at a pre-crimp stage are only compounded if the scaffold is then deformed further during a final crimping to the balloon. As will be appreciated, irregular deformations of scaffold struts can often occur. When struts of a polymer scaffold are irregularly bent or twisted, however, they are more often deemed unacceptable than if this were to occur the scaffold was formed from a metal. Irregular bending or twisting of polymer struts can lead to cracks and fracture, an uncommon occurrence in metal scaffolds. Thus, acceptable irregularities for a crimped metal scaffold are, in many cases, unacceptable for a polymer scaffold.

The solution to the problem of high rejection rates faced by the inventor was quite elusive, for two reasons. First, because there was no available means for tracking the deformation of the polymer scaffold within the crimper, it was not known whether the problem was due to the crimper, a process occurring during fabrication of the scaffold, or the alignment of the scaffold in the crimper. Despite extensive knowledge in the art concerning crimping, no previously proposed crimping-related process known to the inventor, or methods for diagnosing a crimping problem shed any light on a solution to the problem. Second, the art has dealt rather extensively with improving crimping processes for metal scaffolds. However, the assumptions made about the scaffold when improving crimper processes, or problem-solving, have ignored, or underestimated significant differences between polymer and metal scaffolds. First, irregular deformations of metal scaffold struts, while not desirable, are often acceptable. The same is not true of a polymer scaffold due to its material properties. Second, polymer scaffolds are more susceptible to irregular deformations than metal scaffolds due to the reduced space between polymer struts vs. metal struts (polymer struts are thicker than metal struts having equivalent stiffness properties). The existing art pertaining to crimpers fails to adequately account for these differences.

It was discovered that electrostatic charges that can develop on a polymer scaffold was a key cause for scaffold damage. The influence of this charge was noticed when the scaffold, supported on the scaffold support, was visually inspected. One end of the scaffold was raised slightly higher off the scaffold support than the opposite end. When pressure was applied to the raised end of the scaffold, e.g., by applying finger pressure, then this pressure was released, the end returned to its raised position. When the scaffold was sprayed by a de-ionizing spray, the upwards bias of the scaffold end disappeared. It was concluded, therefore, that the raised end was caused by an electro-static charge on the scaffold.

The ability of material to surrender its electrons or absorb excess electrons is a function of the conductivity of the material. For example, a pure conductor, such as copper, has a rigid molecular construction that will not permit its electrons to be moved about freely. Non-conductive materials, such as a polymer, e.g., PLLA, have a molecular construction that is more easily disrupted by friction, heat or pressure applied to the material to induce a charge on the surface. If the conductivity of the surface is controlled, then a static charge can be avoided. Adding surface conductivity to the polymer can prevent the buildup of static electricity. This is normally accomplished by use of additives such as moisture and anti-static sprays. Typical anti-static sprays are made from a soap based material diluted in a volatile solvent. The solvent evaporates leaving a conductive coating on the surface of the material. The polymer surface becomes conductive. As long as the coating is not disturbed, a static charge can be avoided. Electric deionizers, known in the art, may also be used.

Scaffolds designated for pre-crimping were deionized by an electric deionizer before pre-crimping, to determine whether the removal of a static charge would have an effect on how the scaffold was crimped. When the deionized scaffolds were removed from the crimper, there were fewer instances of irregular deformations in the struts. Based on this discovery, it was thought that electro-static charges, which caused the scaffold to misalign with the crimper, induced non-uniform resistance to deformation within the crimper to cause struts to bend and twist irregularly when being crimped. The presence of a static charge and resulting misalignment of a scaffold that might occur due to the presence of this charge was not surprising (the scaffold is made from a polymer). However, the effect on crimping due to the presence of this charge and resulting misalignment was quite surprising. A relatively minor change to the crimping process, i.e., deionizing the scaffold just prior to crimping, was disproportionate to the change in results produced.

About 600 scaffolds were evaluated using a pre-crimping process that included a deionization step. With this step included in the pre-crimping process the rejection rate was reduced from 60% to less than 30% (about 26%)—a dramatic improvement.

To achieve similar results, the scaffolds may be sprayed or immersed in a deionization solution, or an electric deionizer may be used, before being fitted onto a support. The scaffold support 20, e.g. surfaces of the balloon, and/or scaffold may be sprayed just prior to inserting the scaffold into the crimping device. Further, following any adjustment of the scaffold on the support the scaffold may be sprayed again by a deionization solution since any sliding motion between the surfaces may again cause a static charge buildup. According to one embodiment a pre-crimp process for a deionized scaffold is followed by a final crimp process that includes a second deionization step just after final alignment. After the scaffold has been aligned with balloon markers the scaffold and balloon are deionized by an electric deionizer to remove any possible static buildup between the surfaces that occurred during final alignment.

Based on the foregoing, it was hypothesized that other refinements to the alignment of a polymer scaffold within a crimper might further reduce rejection rates. In addition to deionizing the polymer scaffold when it sits on the scaffold support, e.g., rod, mandrel or catheter, the base that holds the scaffold support in place was modified to enable more precise alignment with the crimper. As it turns out, better alignment of the scaffold support position relative to the crimper also improved results. From this finding, it was confirmed that, in general, a misaligned polymer scaffold is more susceptible to damage within a crimper than a corresponding misaligned metal stent. A polymer scaffold that has a "slight" misalignment within the crimper has a far greater chance of becoming damaged.

The known art provides apparatus for aligning and supporting a scaffold on a scaffold support when it is placed between the jaws of a crimper. Such commercial crimping systems are well known. One such crimping system provides a base support having a gripper or jaws for holding one end of the scaffold support to the base. For example, a lock knob is used to tighten-down the scaffold support to hold it in place. A scaffold is then placed on the end of the scaffold support, or the scaffold is placed on the scaffold support before the scaffold support is secured to the base. The supported scaffold is then inserted into the crimper by moving the end of the scaffold support into the jaws of the crimper. The engagement of the crimper jaws on the scaffold using this arrangement has proved satisfactory in the past. But when faced with the unexplained number of rejected scaffolds crimped using this crimping system and the discovery that more precise alignment is needed for a polymer scaffold during crimping, it was suspected that an improvement in alignment might yield still better results for a pre-crimp process, in addition to deionizing the scaffold before crimping.

A base that uses a lock knob, or mechanical lock is susceptible to creating conditions where the scaffold support is not sufficiently aligned with the crimper. For example, if the knob is tightened down too much, or not enough, the scaffold support can be orientated slightly up or down. This arrangement can frequently produce a slight misalignment of the scaffold with the crimper jaws, which can result in an irregular deformation during diameter reduction. The degree of this misalignment by an operator, for example, when performing routine scaffold alignment for a pre-crimp, was previously thought slight and not of significance to suspect that an improvement in scaffold alignment was necessary. However, the inventor's discovery concerning alignment within a crimper for a polymer scaffold, as opposed to a metal scaffold, revealed that precise alignment was more important than previously thought.

Figure 3:
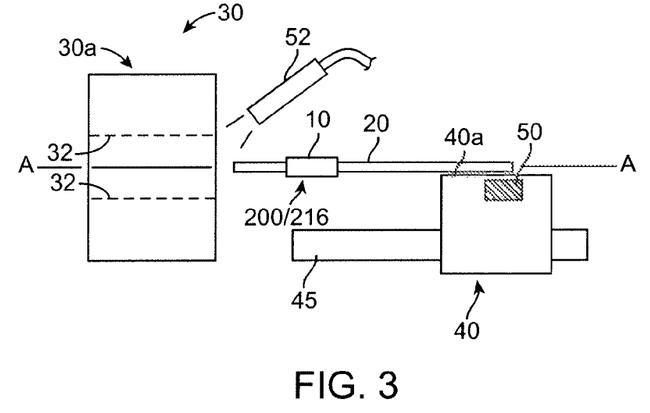
FIG. 3 is a schematic view showing a first embodiment of a scaffold alignment apparatus and method.

FIG. 3 shows an alignment carriage for a polymer scaffold. The alignment carriage includes carriage 40 include an alignment surface 40a and a magnetic element 50 disposed on or near the surface 40a. The carriage is movable towards/away from a crimping device 30. The axis of alignment is depicted as axis A. The scaffold 10, e.g., scaffold with a stent pattern 200 or intermediate pattern 216 (described below) is supported on a support 20, which is held along axis A by carriage 40.

The carriage 40 is moved towards and away from the crimping device 30, e.g., an iris crimper having a crimper head portion 30a and jaws 32, along a rail 45 in such a manner that support 20 remains parallel with axis A and the central axis of the crimping device 30. When alignment is achieved, all exterior surfaces, proximal and distal, of the scaffold 10 receive the jaws 32 at about the same time. To achieve this condition, the scaffold 10 is disposed within the head 30a and equidistant between jaws 32 so that there is a near perfect, uniform radial compression of the scaffold to avoid irregular twisting or bending of scaffold struts. Alignment of surface 40a with axis A, so that when support 20 is flush with surface 40a its central axis lies on axis A and extends parallel thereto, may be accomplished using a well-known laser alignment system or other suitable device. The support 20, when placed on surface 40a is securely held thereto by a magnetic force of attraction between element 50 and a metal portion of the support 20. The support 20 need only be laid flush with the surface 40a. A groove formed on surface 40a and extending parallel to axis A may be used to assist with aligning support 20 properly on surface. There is no mechanical adjustment needed to hold the support 20 to the base 40. As such, there is less tendency for a scaffold support to become misaligned relative to axis A by an operator.

An anti-static air-gun or nozzle 52 is directed towards the crimper heads and scaffold 10 to remove any static charge existing on the polymer scaffold 10 and/or in the crimper during the pre-crimp. The air gun may be passed over the scaffold before it is inserted into the crimper. Or the air gun may be disposed adjacent the opening (as shown) and run during the pre-crimp. The carriage 40 travels along the rail 45 to place the end of the support 20 and scaffold 10 within the head 30a, and then remove the scaffold 10 and support 20 from the head 30a after pre-crimp.

Figure 4:
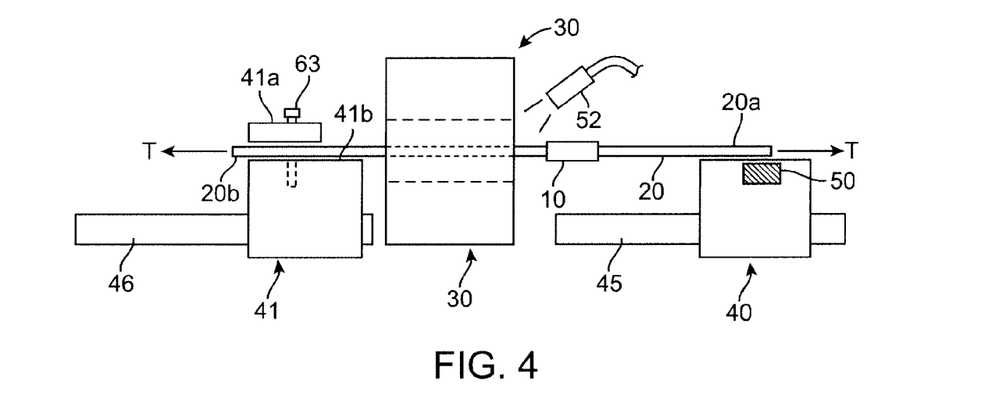
FIG. 4 is a schematic view showing a second embodiment of a scaffold alignment apparatus and method.

In an alternative embodiment, a second base support 41 may be provided at the opposite side of the crimper 30 to support end 20b of the scaffold support 20, as depicted in FIG. 4. This arrangement supports the scaffold support at both ends 20b, 20a as opposed to the cantilever-type support depicted in FIG. 3. The first base support 40 as located on one side of the crimper 30 and the second base support 41 is located at the opposite side of the crimper 30. Each may be controlled by the same rail mechanism, which moves the bases 40/41 together from side to side. Second base support 41 may be constructed as part of an alignment carriage like the alignment carriage described in connection with FIG. 3. Thus, base support 41 may be part of an alignment carriage movable along a rail 45 and including a surface (not shown) to receive the end 20b on a flat or grooved surface. A magnet may also be disposed on or near this surface to hold the end 20b of the scaffold support 20 in place. When aligning scaffold support 20 and scaffold 10 the surfaces are brought together to support scaffold support 20 at ends 20a, 20b. Then both bases 40, 41 are moved right to left in FIG. 4 to place the aligned scaffold 10 within the crimper 30. Referring to FIG. 4, alternatively, second base 41 may have a clamp with an upper bearing surface portion 41a and lower bearing surface 41b. A knob or screw 43 is used to bring the two surfaces 41a, 41b together to grip the end 20b. An anti-static air gun 52 is used to remove static charge. The length of surface 40a and magnet strength and corresponding length of surface 40a on the left side (if a clamp is not used) is such that both support ends 20a, 20b are restrained in a fixed-type arrangement (i.e., they are not pinned at the ends). Thus, the end 20a and end 20b cannot rotate about any axis because it is fixed. This arrangement facilitates the degree of precision the inventor found is sometimes needed to improve polymer scaffold crimping.

In either of the embodiments described in connection with FIG. 4, or in connection with FIG. 5, the base supports 40, 41 may be operated to apply a tension force to the scaffold support 20 (by moving the bases 40, 41 slightly apart). By applying a tension T, one can remove any possible sagging of the scaffold support 20, as may be necessary due to an extended length of the scaffold support 20 needed to support both ends 20a, 20b on opposite sides of the crimper 20. Additionally, with regards to the embodiments described in relation to FIG. 4 and embodiments associated with FIG. 5, more than the stents illustrated may be disposed on the support 20 due to the fixed support (as opposed to cantilever at one end). Since the support 20 is supported at both ends the support 20 should not deflect in the middle due to the weight of the scaffolds, or its own weight. A tension T may also be applied if needed to maintain precise alignment with the crimper axis. Thus, in the embodiment depicted in FIG. 4 two scaffolds may be crimped at the same time.

Figure 5:
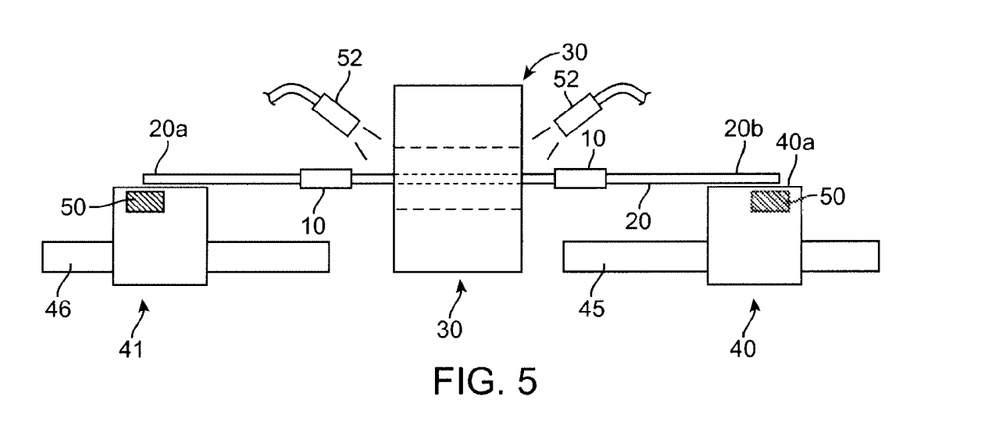
FIG. 5 is a schematic view showing a third embodiment of a scaffold alignment apparatus and method.

FIG. 5 shows another embodiment of a scaffold alignment system. Two bases 40, 41 are disposed on opposite sides of the crimper 30. Each base includes a magnet 50 for retaining the ends 20a, 20b to the bases 40, 41 respectively. The alignment is achieved by placing the ends 20a, 20b on the bases 40, 41 as before in FIG. 3. In this embodiment, a first and second scaffold 10 is located on opposite sides of the crimper 30 so that both scaffolds may be crimped, one after another. The scaffold 10 on the right in FIG. 5 is moved into the crimper 30 by displacing the bases 40, 41 along rails 45, 46 from right to left. The air gun 52 is used to remove static charge. After this pre-crimp is complete, the scaffold 10 on the left of the scaffold is pre-crimped by moving the bases 40, 41 from left to right. A second or the same anti-static air gun 52 is used to remove a static charge. A tension T may be applied to support 20 as in the embodiment depicted in FIG. 4.

According to the disclosure, a scaffold fabrication, pre-crimping and final crimping process including the alignment steps just described is also provided. The scaffold fabrication process includes forming the scaffold from an expanded tube to increase its strength and stiffness characteristics. The crimping process is, preferably, multi-step and includes a selection of a narrow temperature range for heating the scaffold, selected according to the glass transition temperature for the polymer.

A "glass transition temperature," Tg, is the temperature at which the amorphous domains of a polymer generally change from a brittle, vitreous state to a solid deformable or ductile state at atmospheric pressure. In other words, the Tg corresponds to the temperature where the onset of noticeable segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Poly(L-lactide) (PLLA) and Poly(lactide-co-glycolide) (PLGA) are examples of a class of semi-crystalline polymers that may be used to form the scaffold structure described herein. PLLA is a homo-pomonomer, while PLGA is a co-polymer. The percentage of Glycolic Acid (GA) in a scaffold constructed of PLGA may be between 0-15%. For PLLA, the onset of glass transition occurs at about 55° C. For PLGA, an increase of GA from about 0% to 15% lower range for Tg to about 50° C.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the scaffold structural members cut from the tube without this expansion. The degree of radial expansion that the polymer tube undergoes characterizes the degree of induced circumferential molecular or crystal orientation. In a preferred embodiment, the radial expansion ratio or RE ratio is about 400% of the starting inner tube diameter and the axial expansion ratio or AE ratio is about 150% of the starting tube length.

The above scaffold's outer diameter may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the scaffold to dislodge in the vessel. Further, since a vessel wall cannot be assumed as circular in cross-section, and its actual size only an approximation, a physician can choose to over-extend the scaffold to ensure it stays in place. For this reason, it is preferred to use a tube with a diameter larger than the expected deployed diameter of the scaffold.

In one embodiment the ratio of deployed to fully crimped diameter is about 2.5. In this embodiment, the crimped diameter corresponds to an outer diameter that is only about 40% of the starting diameter. Hence, when deployed the drug eluting scaffold is expected to increase in size up to about 2.5 times its stowed or crimped diameter size.

In one particular example, a scaffold is formed from a biaxially expanded tube having an outer diameter of 3.5 mm, which approximately corresponds to a deployed diameter (the scaffold may be safely expanded up to 4.0 mm within a lumen). When crimped on the balloon, the scaffold has an outer diameter of 1.3 mm, or about 37% of the starting tube diameter of 3.5 mm.

As discussed earlier, fabrication of a balloon-expanded polymer scaffold presents challenges that are not present in metallic scaffolds. One challenge, in particular, is the fabrication of a polymer scaffold, which means the load bearing network of struts including connectors linking ring elements or members that provide the radial strength and stiffness needed to support a lumen. In particular, there exists an ongoing challenge in fabricating a polymer scaffold capable of undergoing a significant degree of plastic deformation without loss of strength. In the disclosed embodiments, a polymer scaffold is capable of being deformed from a crimped diameter to at least 2.5 times the crimped diameter without significant loss of strength. Moreover, the polymer scaffold is retained on a delivery balloon with a retention force that is significantly higher than previous methods of scaffold retention for a polymer scaffold.

There is a certain degree of beneficial movement between interconnected polymer chains of a scaffold structure heated to temperatures just below Tg of the polymer when the scaffold is being crimped to a balloon, versus the same scaffold crimped to the balloon at a lower temperature, such as room temperature. For example, for a controlled temperature of between about 48° C. and 54° C., 48-50° C. or 48° C. it was found that a PLLA scaffold crimped to a balloon exhibited noticeable improvement in the retention force of the scaffold on the balloon, while not concomitantly producing unacceptable side effects for the deployed scaffold, e.g., excessive cracking, void formation, fracture and/or loss of memory in the material affecting its deployed radial strength qualities.

One problem encountered with fabrication of a scaffold for delivery to a site in a body using a balloon is the ability of the scaffold to be safely crimped to the balloon so that an adequate retention force is established between the scaffold and balloon. A "retention force" for a scaffold crimped to a balloon means the maximum force, applied to the scaffold along the direction of travel through a vessel, which the scaffold-balloon is able to resist before dislodging the scaffold from the balloon. The retention force for a scaffold on a balloon is set by a crimping process, whereby the scaffold is plastically deformed onto the balloon surface to form a fit that resist dislodgment of the scaffold from the scaffold. Factors affecting the retention of a scaffold on a balloon are many. They include the extent of surface-to-surface contact between the balloon and scaffold, the coefficient of friction of the balloon and scaffold surfaces, and the degree of protrusion or extension of balloon material between struts of the scaffold. For a metal scaffold there are a wide variety of methods known for improving the retention force of a scaffold on a balloon via modification of one or more of the foregoing properties; however, many are not suitable or of limited usefulness for a polymeric scaffold, due to differences in mechanical characteristics of a polymer scaffold verses a metal scaffold as discussed earlier. Most notable among these differences is brittleness of the polymer material suitable for balloon-expanded scaffold fabrication, verses that of a metal scaffold. Whereas a metal scaffold may be deformed sufficiently to obtain a desired retention force, the range of deformation available to a polymer scaffold, while avoiding cracking or fracture-related problems, by comparison, is quite limited.

For polymeric scaffolds, the glass transition temperature (Tg) of its matrix material has to be higher than physiological temperatures (37° C.) in order to maintain radial strength after implantation. A scaffold formed from PLLA has a Tg of about 55-60° C. When a PLLA scaffold is crimped to a balloon at around 25° C., a free polymer chain movement hardly occurs. As a consequence, the PLLA is brittle and susceptible to crack formation. Moreover, at this temperature, well below Tg, the scaffold will tend to recoil or revert towards its starting diameter of the tube, to a certain degree, due to the memory in the material. In other others, when the scaffold is deformed during crimping, the induced strain in the polymer matrix will cause the scaffold to enlarge to a certain degree once the crimping force is removed, since there will be some percentage of elastic deformation when the scaffold is crimped to the balloon, which causes the scaffold to revert towards its original diameter when the crimping force relieved. This degree of elastic recoil, so to speak, limits the amount of retention of the scaffold on the balloon since the degree of contact between scaffold and balloon is reduced. Stated somewhat differently, when there is elastic recoil to a larger diameter, the normal force the scaffold imparts on the balloon while the crimping force is applied, which is proportional to magnitude of the retention force, decreases once the crimper is removed due to the percentage of elastic recoil in the scaffold.

Figure 1:
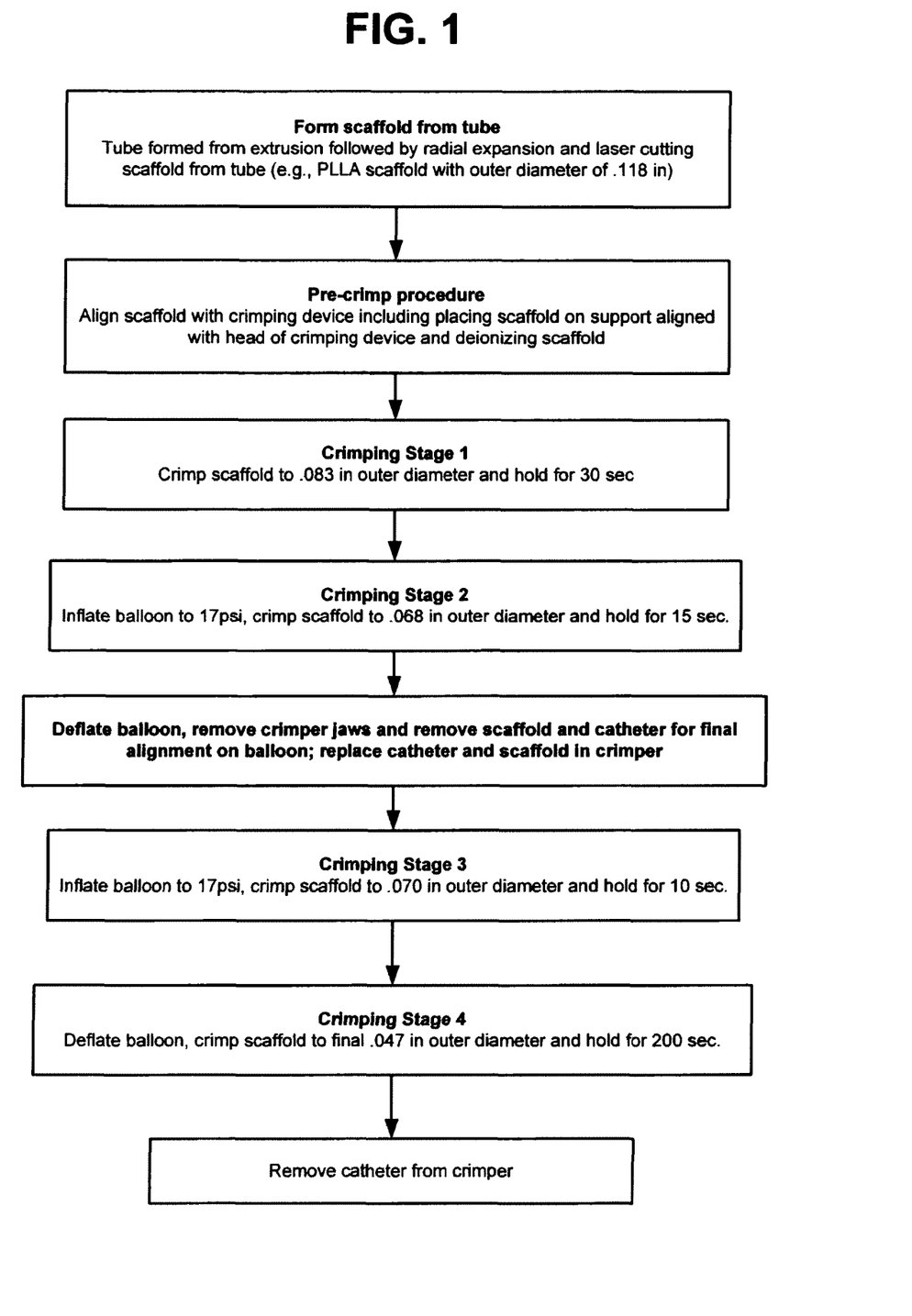
FIG. 1 shows a process for fabricating a scaffold of a polymer scaffold and crimping the fabricated scaffold to a balloon according to the invention.
Figure 2:
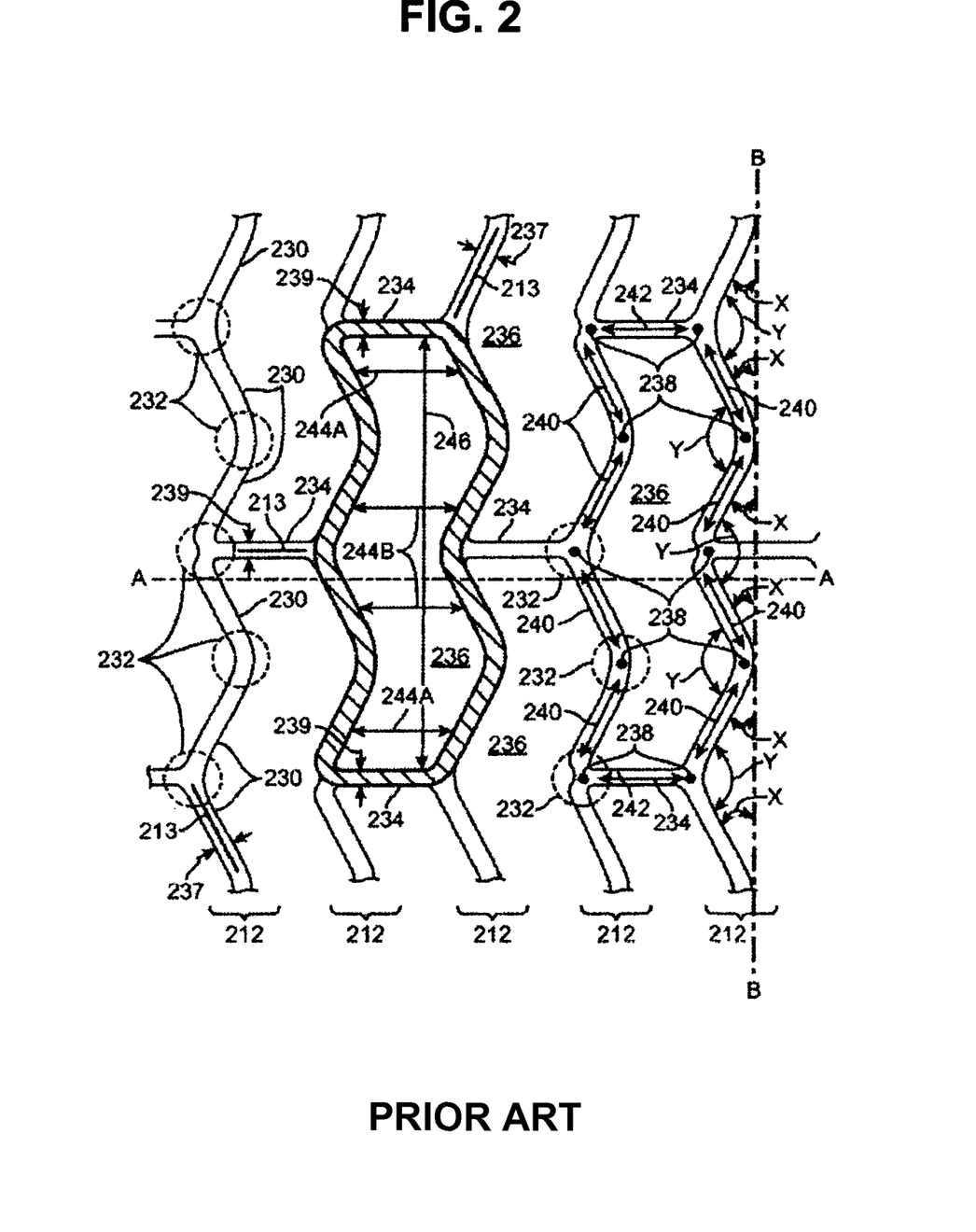
FIG. 2 is planar view of a portion of a polymer scaffold that was crimped to a balloon according to aspects of the invention. This view describes the scaffold pattern of the load-bearing structure of the scaffold of the fully deployed scaffold that is crimped to a balloon according to the process of FIG. 1.

FIG. 1 is a process diagram illustrating the steps used to fabricate a polymer scaffold and crimp the scaffold to a balloon. In this example, a scaffold was formed from a radially expanded tube of PLLA. The scaffold had a strut pattern as shown in FIG. 2. The struts had a thickness of about 0.152 mm and the balloon used was a PEBAX balloon. An iris crimper was used to pre-crimp and final crimp of the scaffold to the balloon.

A crimping process may proceed as follows. In preparation for a pre-crimp scaffold, the scaffold is deionized and aligned with the crimper 30 using the alignment system of FIG. 3. Then, the crimp head diameter is moved to an intermediate position that is larger than the scaffold starting outer diameter (OD). The temperature of the jaws is raised to, or to about 48° C. and is allowed to stabilize at that temperature. The scaffold is pre-crimped then removed from the crimper.

In the embodiments, an anti-static filtered air gun is used to deionize the scaffold before and/or during pre-crimping. Before pre-crimp, the anti-static air gun is passed over the scaffold front to back to remove static charges on the scaffold. In one case, the anti-static filtered air gun is applied for 10 seconds to 1 minute along the scaffold. In another embodiment, the air gun deionizes the scaffold during pre-crimping. The anti-static filtered air gun is applied for 10 seconds to 1 minute along the scaffold.

A delivery catheter (holding the balloon) is chosen with the correct size to fit the scaffold. The scaffold is placed onto the balloon of the catheter with the distal portion of the scaffold aligned with the distal portion of the catheter. The catheter is then placed onto the sliding alignment carriage 40. A final adjustment is made to the scaffold to position it between balloon markers on the catheter. The scaffold and catheter is moved into the crimp jaws, by sliding the carriage 40 forward along the rail 45.

The cycle is initiated by the operator. As an example, for a 3.0×18 mm scaffold, the ID of the crimp head moves to a diameter of 0.083" where it remains for 30 seconds. This is stage 1. The system moves automatically to stage 2 where the head moves to an ID of 0.068" and is held for 15 seconds. During this stage, the balloon catheter is inflated to 17 psi. After this stage is complete, the balloon is deflated and the crimp head is opened to allow the catheter to be removed. The scaffold receives a final alignment to the balloon markers. The scaffold and balloon are placed back into the crimp head. The operator initiates stage 3 where the head is reduced to 0.070" diameter for 10 seconds. During this stage 3, the balloon is also inflated to 17 psi. Once complete, the machine moves automatically to the stage 4, where the balloon is deflated and the crimp head ID is reduced to 0.047" and is held for 200 seconds. When this fourth and final stage is complete, the head opens and the catheter and scaffold removed. The scaffold is retained on the balloon and is immediately placed into a sheath.

As noted above, in a preferred embodiment a scaffold has the scaffold pattern described in U.S. application Ser. No. 12/447,758 (US 2010/0004735) to Yang & Jow, et al. Other examples of scaffold patterns suitable for PLLA are found in US 2008/0275537.

FIG. 2 shows a detailed view of an intermediate portion 216 of a strut pattern 200 depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B-B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the scaffold is deployed. Having the interior angle be less than 180 degrees allows the scaffold to be crimped while minimizing damage to the scaffold struts during crimping, and may also allow for expansion of the scaffold to a deployed diameter that is greater than its initial diameter prior to crimping. Link struts 234 connect the rings 212. The link struts 234 are oriented parallel or substantially parallel to a bore axis of the scaffold. The ring struts 230, hinge elements 232, and link struts 234 define a plurality of W-shape closed cells 236. The boundary or perimeter of one W-shape closed cell 236 is darkened in FIG. 2 for clarity. In FIG. 2, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 2, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 of the strut pattern. The distances 242 are the same or substantially the same for each link strut 234. The ring struts 230 have widths 237 that are uniform in dimension along the individual lengthwise axis 213 of the ring strut. The ring strut widths 237 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 2, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236.

It will be appreciated from FIG. 2 that the strut pattern for a scaffold that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the scaffold central axis. The link struts 234 are oriented parallel or substantially parallel to the scaffold central axis. The link struts 234 connect the rings 212 together. The link struts 234 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method, comprising the steps of:
using a crimper having jaws;
performing a pre-crimp of at least one polymer scaffold including the steps of
deionizing the scaffold,
aligning a support with the crimper, the support comprising:
a movable carriage, and
a rod or a mandrel;
disposing the scaffold on the support,
using the support, placing the scaffold within the crimper, and
reducing the diameter of the scaffold; and
after performing the pre-crimp, crimping the scaffold to a balloon of a balloon catheter.

2. The method of claim 1, wherein the scaffold is formed from a radially-expanded tube and includes a circumferential series of closed cells having a W-shape and linear link struts connecting the W-shape cells.

3. The method of claim 1, wherein the scaffold is removed from the crimper after the pre-crimp step and aligned on the balloon before crimping the scaffold to the balloon.

4. The method of claim 1, wherein the movable carriage is a first carriage and the support further comprises a second carriage, and
wherein the aligning a support with the crimper includes affixing a first and second end of the support to the first and second carriages having respective first and second surfaces adapted for supporting the first and second ends by a magnetic force.

5. A method, comprising the steps of:
using a crimper having jaws;
performing a pre-crimp of a plurality of polymer scaffolds including the steps of
deionizing the scaffolds,
aligning a support with the crimper, the support comprising:
a movable carriage, and
at least one of a rod and a mandrel,
disposing the scaffolds on the support,
using the support, placing each of the scaffolds within the crimper, and
reducing the diameters of each of the scaffolds; and
after performing the pre-crimp, crimping each of the scaffolds to balloons of balloon catheters.

6. The method of claim 5, wherein each of the plurality of scaffolds are reduced in diameter, one after another, while the plurality of scaffolds are disposed on the support.

7. The method of claim 1, wherein the deionizing the scaffold includes using an anti-static air gun.

8. The method of claim 1, wherein the scaffold is cut from a tube comprising the polymer.

9. The method of claim 1, wherein the scaffold has a final crimped diameter when crimped to the balloon and a deployed diameter of the scaffold is at least 2.5 times greater than the final crimp diameter.

10. The method of claim 1, wherein after crimping to the balloon the scaffold has a crimped diameter that is at least 2.5 times smaller than the scaffold's diameter before the pre-crimp.

11. The method of claim 1, wherein the scaffold further includes rings formed by ring struts, wherein prior to crimping a pair of ring struts adjoined at a crown are each orientated at an angle of between 20 and 30 degrees with respect to an axis perpendicular to a longitudinal axis of the scaffold, and an angle of between 120 and 130 degrees spans between the adjoined ring struts.

12. The method of claim 1, further including the step of aligning the support and scaffold with the crimper jaws using a means for alignment.

13. The method of claim 12, wherein the means for alignment includes the mandrel extending through the crimper and the mandrel is supported at both a first end and a second end of the mandrel.

14. The method of claim 12, wherein the means for alignment includes the movable carriage having a groove that is aligned with a central axis of the crimper when the support is aligned with the crimper.

15. The method of claim 5, wherein each of the scaffolds are crimped to the respective balloons at the same time.

16. The method of claim 1, wherein the support further includes the balloon catheter received over the rod or mandrel, and the scaffold is disposed on the balloon during the pre-crimp step.

* * * * *